US012471983B2

(12) United States Patent
Kitamura et al.

(10) Patent No.: US 12,471,983 B2
(45) Date of Patent: Nov. 18, 2025

(54) TREATMENT INSTRUMENT, TREATMENT SYSTEM, AND CONTROL METHOD

(71) Applicant: OLYMPUS MEDICAL SYSTEMS CORP., Tokyo (JP)

(72) Inventors: Ojiro Kitamura, Hachioji (JP); Tsuyoshi Hayashida, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 548 days.

(21) Appl. No.: 17/884,208

(22) Filed: Aug. 9, 2022

(65) Prior Publication Data

US 2023/0048211 A1 Feb. 16, 2023

Related U.S. Application Data

(60) Provisional application No. 63/232,412, filed on Aug. 12, 2021.

(51) Int. Cl.
*A61B 18/14* (2006.01)
*A61B 18/00* (2006.01)

(52) U.S. Cl.
CPC .................... *A61B 18/1447* (2013.01); *A61B 2018/00922* (2013.01); *A61B 2018/00946* (2013.01)

(58) Field of Classification Search
CPC ........... A61B 18/1447; A61B 18/1445; A61B 2018/00922; A61B 2018/00946; A61B 2018/1455
See application file for complete search history.

(56) References Cited

U.S. PATENT DOCUMENTS 9,456,863 B2 10/2016 Moua
2016/0375273 A1* 12/2016 Hirai ...................... A61B 17/29 606/29
2018/0310948 A1* 11/2018 Stamm ............... A61B 18/1445
2020/0222109 A1* 7/2020 Stamm ............... A61B 18/1445

* cited by examiner

*Primary Examiner* — Ankit D Tejani
*Assistant Examiner* — Joshua Brendon Solomon
(74) *Attorney, Agent, or Firm* — Morgan, Lewis & Bockius LLP

(57) ABSTRACT

The procedure instrument includes an end effector for treating biological tissue by grasping biological tissue by opening and closing and imparting treatment energy to biological tissue, a fixed handle grasped by an operator, a movable handle for opening and closing the end effector by moving in a direction close to and away from the fixed handle, respectively, and a first switch provided inside the fixed handle and receiving a user operation for imparting treatment energy to the biological tissue from the end effector in response to the movement of the movable handle, and a second switch provided in a state of being exposed outside the fixed handle and receiving a user operation in response to the movement of the movable handle.

20 Claims, 11 Drawing Sheets

TREATMENT INSTRUMENT, TREATMENT SYSTEM, AND CONTROL METHOD

RELATED APPLICATION DATA

This application is based on and claims priority under 35 U.S.C. § 119 to U.S. Provisional Application No. 63/232,412 filed on Aug. 12, 2021, the entire contents of which are incorporated herein by reference.

FIELD OF THE INVENTION

The present invention relates to a treatment instrument, a treatment system, and a control method.

DESCRIPTION OF THE RELATED ART

Conventionally, there has been known a treatment instrument which treats a site of interest by imparting treatment energy, such as ultrasonic energy, to a site to be treated in a biological tissue (hereinafter, referred to as a target site) (see, for example, Patent Document 1). The treatment instrument described in Patent Document 1 includes a fixed handle which is grasped by an operator, and a movable handle which moves in a direction toward and away from the fixed handle. Further, on the side surface of the fixed handle, a switch is provided which is pressed by the movable handle while gripping the movable handle. Then, when the switch is pressed, the procedure energy is imparted to the target site from the treatment instrument under control by a control device provided outside the treatment instrument.

Prior art documents—Patent Document 1: U.S. Pat. No. 9,456,863.

SUMMARY OF THE INVENTION

Problem to be Solved by the Invention

However, in the procedure instrument described in Patent Document 1, there is a case where a switch is erroneously pressed due to pinching of a foreign object between the fixed handle and the movable handle or due to an erroneous holding of the treatment instrument by an operator. In other words, the operator may unintentionally contact the switch to impart treatment energy to the target site.

In view of the foregoing, it is an object of the present invention to provide a treatment instrument, a treatment system, and a control method which can avoid unintentionally imparting treatment energy to a target site by an erroneous operation.

Means for Solving the Problem

In order to solve the above problems and achieve the purpose, a procedure instrument according to the present invention includes an end effector which grasps biological tissue by opening and closing and treats the biological tissue by imparting treatment energy to the biological tissue, a fixed handle which is grasped by an operator, a movable handle which opens and closes the end effector by moving in a direction toward and away from the fixed handle, respectively, and a first switch which is provided inside the fixed handle and which accepts a user operation for imparting the treatment energy to the biological tissue from the end effector in response to the movement of the movable handle, and a second switch which is provided in a state of being exposed to the outside of the fixed handle and accepts the user operation in response to the movement of the movable handle.

A treatment system according to the present invention includes a treatment tool for treating a biological tissue, a control device having a processor for controlling the operation of the treatment tool, wherein the treatment tool grasps the biological tissue by opening and closing, and treats the biological tissue by imparting treatment energy to the biological tissue, a fixed handle which opens and closes the end effector by moving in a direction toward and away from the fixed handle, respectively, and a first switch which is provided inside the fixed handle and which accepts a user operation for imparting the treatment energy from the end effector to the biological tissue in response to the movement of the movable handle, and a second switch which is provided in a state of being exposed to the outside of the fixed handle and accepts the user operation in response to the movement of the movable handle. The first switch initiates acceptance of the user operation when the movable handle moves in a direction proximate to the fixed handle and a distance between the fixed handle and the movable handle is at a first distance (or less), and the second switch initiates acceptance of the user operation when the movable handle moves in a direction proximate to the fixed handle and the distance between the fixed handle and the movable handle becomes a second distance, which is different from the first distance, and the processor initiates application of the treatment energy to the biological tissue from the end effector at a time when both the first switch and the second switch have initiated acceptance of the user operation.

A control method according to the present invention is a control method performed by a processor of a control device for controlling the operation of a treatment tool, wherein the treatment tool is provided with an end effector for treating the biological tissue by imparting treatment energy to the biological tissue, a movable handle for opening and closing the end effector by moving in a direction toward and away from the fixed handle, and a first switch provided in the interior of the fixed handle and that imparts the treatment energy from the end effector to the biological tissue in response to the movement of the movable handle by a user operation. The switch is configured to accept the user operation to impart the treatment energy from when the movable handle moves in a direction proximate to the fixed handle and a distance between the fixed handle and the movable handle becomes a first distance, and the second switch is configured to accept the user operation to impart the treatment energy when the movable handle moves in a direction proximate to the fixed handle and a distance between the fixed handle and the movable handle becomes a second distance that is different from the first distance, and the processor initiates application of the treatment energy to the biological tissue from the end effector at a time when both the first switch and the second switch have accepted of the user operation.

Effect of the Invention

According to the treatment instrument, the treatment system, and the control method according to the present invention, it is possible to avoid unintentionally imparting the treatment energy to the target site by an erroneous operation.

DETAILED DESCRIPTION OF THE PREFERRED EMBODIMENT(S)

Modes for Carrying Out the Invention

Figure 1:
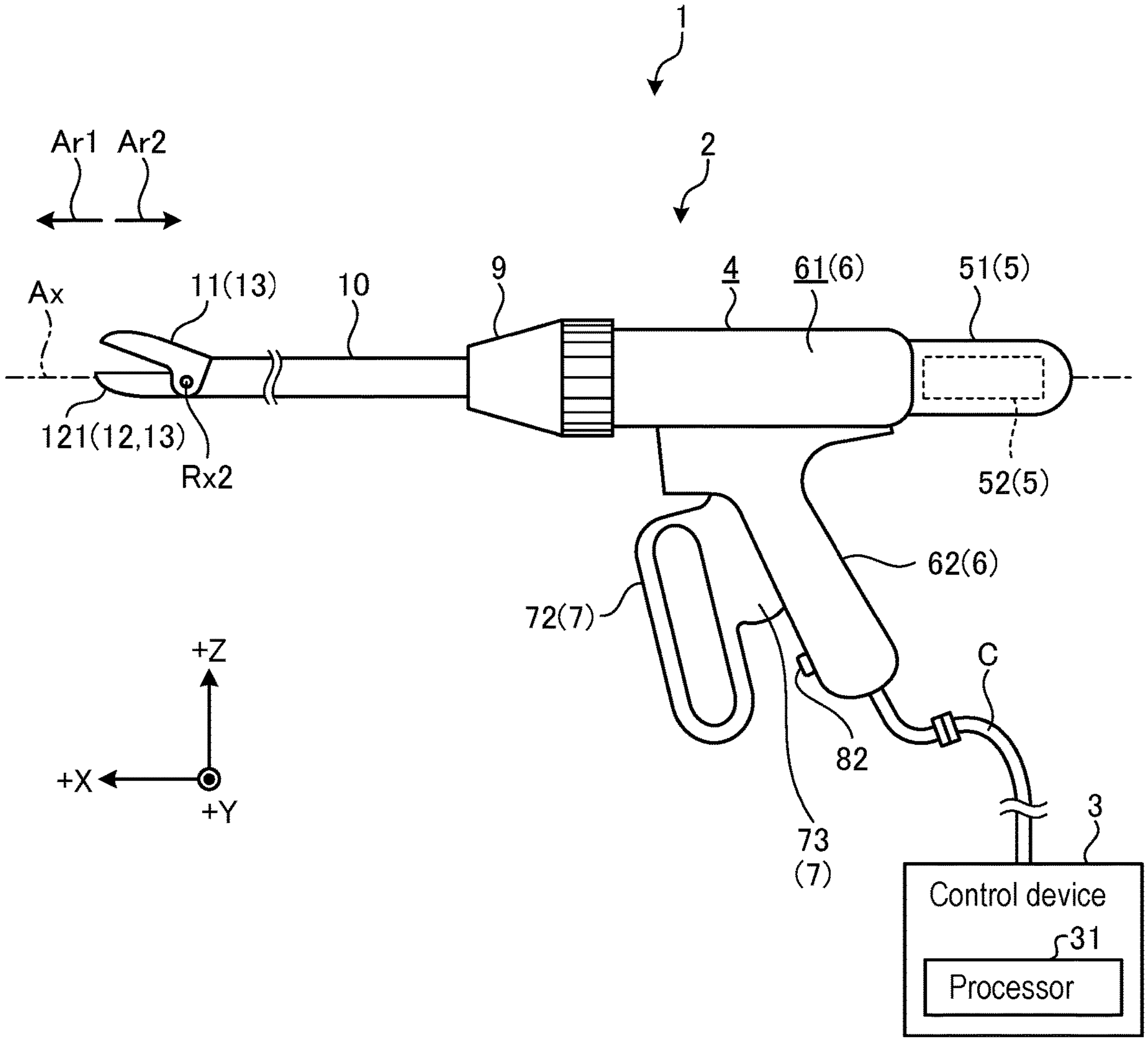
FIG. 1 is a diagram illustrating a treatment system according to an embodiment.

Hereinafter, embodiments for carrying out the present invention (hereinafter, embodiments) will be described with reference to the accompanying drawings. Note that the present invention is not limited by the embodiments described below. In addition, in the description of the drawings, the same parts are denoted by the same reference numerals.

Schematic Configuration of the Treatment System

FIG. 1 is a diagram illustrating a treatment system 1 according to an embodiment. The treatment system 1 treats the target site by imparting treatment energy to a site to be treated in a biological tissue (hereinafter, described as a target site). Note that the procedure energy in the present embodiment is ultrasonic energy and high frequency energy, but embodiments can include other procedure energies, such as thermal energy. Further, a treatment operation that can be performed by the treatment system 1 is a treatment operation such as coagulation (sealing) of a target site or incision of a target site, but other treatment operations can be conducted with the treatment system, such as grasping, exfoliating, and incising. In addition, treatment operations, such as coagulation and incision, may be performed simultaneously. The treatment system 1 comprises a treatment instrument 2 and a control device 3, as shown in FIG. 1

Structure of the Procedure Device

In the following, in describing the configuration of the treatment instrument 2, the X-axis, Y-axis, and Z-axis are mutually orthogonal, as shown by the XYZ coordinate axis in FIG. 1. The X-axis is an axis parallel to the central axis Ax of the shaft 10 (FIG. 1), the Y-axis is an axis perpendicular to the plane of the paper, and the Z-axis is an axis along the vertical direction of FIG. 1. In addition, in the following, one side along the central axis Ax (+X-axis side) is described as a distal end side Ar1, and the other side (−X-axis side) is described as a proximal end side Ar2.

The treatment instrument 2 is an ultrasonic treatment instrument which treats the target site by imparting ultrasonic energy and high frequency energy to the target site. The treatment instrument 2 comprises a handpiece 4 and an ultrasonic transducer 5, as shown in FIG. 1.

The handpiece 4 includes a fixed handle 6, a movable handle 7, a first switch 81 (see FIG. 2), a second switch 82, a rotary knob 9, a shaft 10, a jaw 11, and a vibration transmission member 12, as shown in FIG. 1.

The fixed handle 6 supports the entire treatment instrument 2. As shown in FIG. 1, the fixed handle 6 includes a substantially cylindrical case body 61, which is coaxial with the central axis Ax, and a handle body 62, which extends from the case body 61 to the −Z-axis side (in FIG. 1, the lower side) and is grasped by an operator. As shown in FIG. 1, the movable handle 7 includes a handle base 71 (see FIG. 2), an operation unit 72, and a connecting portion 73. Handle base 71 is located inside the fixed handle 6. The handle base 71, with respect to the fixed handle 6, is rotatably supported about a first rotational axis Rx1, which is parallel to the Y-axis (see FIG. 2). As shown in FIG. 1, the operation unit 72 is located outside the fixed handle 6 and is a portion for receiving the closing operation and the opening operation by an operator. Connecting portion 73 is disposed across the inside and outside of the fixed handle 6 and is a portion for connecting the handle base 71 and the operation unit 72.

Figure 2:
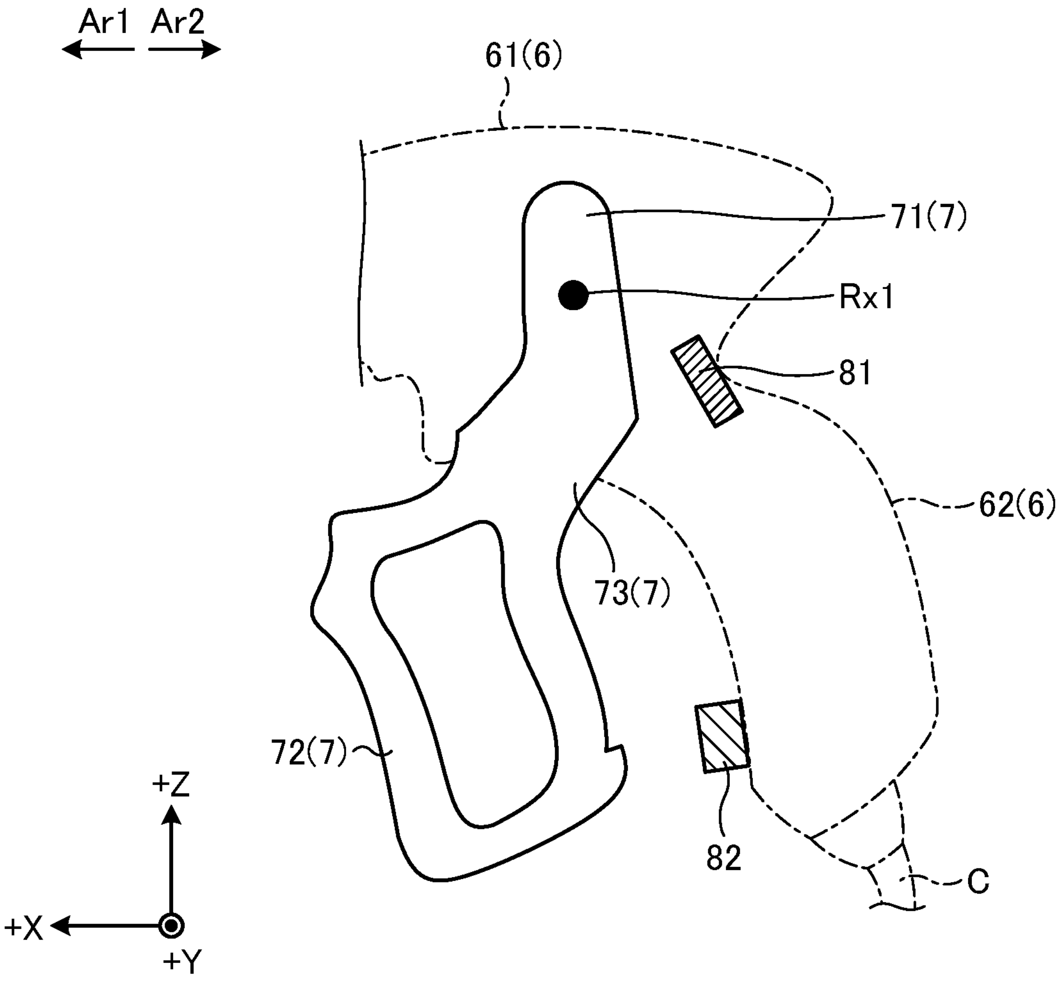
FIG. 2 is a diagram illustrating the arrangement position of the first and second switches.

The movable handle 7 accepts a closing operation and an opening operation, which are user operations made by the operator, such as a medical professional like a doctor or an assistant. Here, the closing operation means an operation in which an operator grips the movable handle 7, such as operation unit 72, with a finger while placing the palm of the hand on the fixed handle 6, such as the handle body 62. In addition, the opening operation means an operation of releasing the grasping force of the operator. In response to the closing operation, the movable handle 7 moves in a direction toward the handle body 62 by rotating about the first rotary shaft Rx1. In response to the opening operation, the movable handle 7 moves in a direction away from the handle body 62 by rotating about the first rotary shaft Rx1 in response to a biasing force from the biasing member, such as a spring provided inside the fixed handle 6, FIG. 2 is a diagram illustrating an arrangement of the first and second switches 81 and 82. As shown in FIG. 2, the first switch 81 is provided inside the fixed handle 6. The first switch 81 accepts a procedure operation which is a user operation for imparting treatment energy to the target site in response to the movement of the movable handle 7. The second switch 82 is provided with a portion externally exposed from the side surface of the handle body 62 on the +X axis side, as shown in FIG. 1 or FIG. 2, and accepts the treatment operation described above.

Note that the relationship between the operation state of the first and second switches 81 and 82 and the state in which the procedure energy is imparted to the target site (hereinafter, described as an output state) will be described in "Relationship between the operation state and the output state of the first and second switches" described later.

Rotary knob 9 has a substantially cylindrical shape or conical shape that is coaxial with the central axis Ax, as shown in FIG. 1, is provided on the distal end-side Ar1 of the case body 61. The rotary knob 9 accepts a rotation control, which is a user operation by an operator. By the rotation control, the rotary knob 9 rotates about the central axis Ax with respect to the case body 61. Further, in addition to the rotary knob 9 being rotatable, the shaft 10, the jaw 11, and the vibration transmission member 12 also rotates about the central axis Ax.

Shaft 10 is a cylindrical pipe made of a conductive material such as metal. Further, the end portion of the distal end-side Ar1 of the shaft 10 includes the jaw 11, which is rotatably supported about a second rotational axis Rx2 extending in a direction perpendicular to the paper surface of FIG. 1. Here, although not shown specifically, an opening and closing mechanism for rotating the jaw 11 around the second rotary shaft Rx2 in response to the opening operation and closing operation to the movable handle 7 by an operator is provided in the fixed handle 6 and the shaft 10. The jaw 11 opens and closes with respect to the end portion 121 (hereinafter, referred to as the treatment portion 121 (FIG. 1)) on the distal end side Ar1 of the vibration transmission member 12 by the opening and closing mechanism, and grasps the target site between the jaw and the treatment portion 121. In addition, at least a part of the jaw 11 is made of a conductive material.

Vibration transmission member 12 is composed of a conductive material and has an elongated shape extending linearly along the central axis Ax. Further and as shown in FIG. 1, the vibration transmission member 12 is inserted into the shaft 10 in a state where the treatment portion 121 protrudes to the outside. At this time, the end of the proximal end side Ar2 of the vibration transmission member 12 is mechanically connected to the ultrasonic vibrator 52 (FIG. 1) constituting the ultrasonic transducer 5. The vibration transmission member 12 transmits the ultrasonic vibration generated by the ultrasonic transducer 5 from the end of the proximal end side Ar2 to the treatment portion 121. In the first embodiment, the ultrasonic vibration is a longitudinal vibration vibrating in a direction along the central axis Ax.

As shown in FIG. 1, the ultrasonic transducer 5 includes a TD (transducer) case 51 and an ultrasonic transducer 52. TD case 51 supports the ultrasonic vibrator 52 and is detachably connected to the case body 61. The ultrasonic vibrator 52 generates ultrasonic vibration under control by the control device 3. In the first embodiment, the ultrasonic vibrator 52 is constituted by a bolt-clamped Langevin transducer (BLT).

Composition of the Control Device

Control device 3 collectively controls the operation of the treatment instrument 2 by passing operating signals and power through the electrical cable C (FIG. 1). The control device 3 includes a processor 31 which is configured using a Central Processing Unit, a Field-Programmable Gate Array (FPGA), and the like, and controls the operation of the treatment instrument 2 according to a program stored in a storage unit (not shown)

Specifically, the processor 31 detects the operation state of the first and second switches 81 and 82 by an operator by passing a signal through an electric cable C. Then, the processor 31 operates a power supply (not shown) constituting the control device 3 according to the operation state of the first and second switches 81 and 82, and imparts procedure energy to the target site grasped between the jaw 11 and the treatment portion 121. In other words, the control device 3 treats the target site.

For example, when applying ultrasonic energy to the target site, the processor 31 causes the ultrasonic vibrator 52 to supply the driving power from the above-described power source by passing through the electric cable C. Thus, the ultrasonic vibrator 52 generates a longitudinal vibration (ultrasonic vibration) which vibrates in a direction along the central axis Ax. The treatment portion 121 also vibrates at a desired amplitude by the longitudinal vibration. Then, an ultrasonic vibration is applied from the treatment portion 121 to the target site grasped between the jaw 11 and the treatment portion 121. In other words, ultrasonic energy is applied from the treatment portion 121 to the target site.

Further, for example, when imparting high-frequency energy to the target site, the processor 31, high-frequency power is supplied between the jaw 11 and the vibration transmission member 12 from the power supply described above by passing it through the electric cable C. Thus, a high frequency current flows through the target portion grasped between the jaw 11 and the treatment portion 121. In other words, the subject site is imparted with high frequency energy.

The jaw 11 and the treatment portion 121 described above correspond to the end effector 13 (FIGS. 1 and 5).

Relationship Between the Operation State and the Output State of the First and Second Switches Next, the relationship between the operation state and the output state of the second switch 81 and 82, will be described first, for and a case where the closing operation is performed with respect to the movable handle 7 and second, in the case where the opening operation is performed with respect to the movable handle 7.

When Closing Operation is Performed on the Movable Handle

Figure 3A:
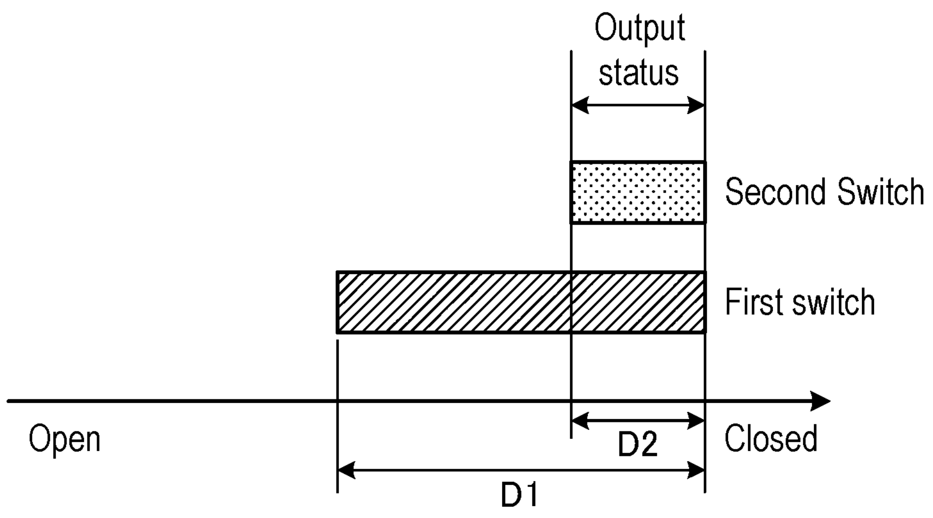
FIG. 3A is a diagram illustrating the relationship between the operation state and the output state of the second switch when the closing operation is performed with respect to the movable handle and FIG. 3B is a process flow diagram illustrating the relationship between the operation state and the output state of the second switch when the closing operation is performed with respect to the movable handle.

FIG. 3A is a diagram for explaining the relationship between the operation state and the output state of the first and second switches 81, 82 when the closing operation is performed with respect to the movable handle 7. When a closing operation is performed on the movable handle 7 and a separation distance between the movable handle 7 (the operation unit 72) and the fixed handle 6 (the handle body 62) becomes progressively smaller and the separation distance becomes a first distance D1 or less (FIG. 3A), the first switch 81 starts accepting the treatment operation. In other words, when the operation unit 72 is moved in a direction toward the handle body 62, i.e., closing, when the separation distance between the operation unit 72 and the handle body 62 becomes the first distance D1, the first switch 81 is enabled, i.e. turned ON. In addition, when a closing operation is performed on the movable handle 7 and a separation distance between the movable handle 7 (operation unit 72) and the fixed handle 6 (handle body 62) becomes progressively smaller and the separation distance becomes a second distance D2 or less (FIG. 3A), where the second distance D2 is smaller than the first distance D1, the second switch 82 starts accepting the treatment operation. In other words, when the operation unit 72 is moved in a direction toward the handle body 62, i.e., closing, when the separation distance between the operation unit 72 and the handle body 62 becomes the second distance D2, the second switch 82 is enabled, i.e., turned ON. When both of the first and second switches 81, 82 are enabled to start accepting the procedure operation, then the processor 31 operates the power supply described above and starts applying the treatment energy to the target site from the end effector 13. That is, as shown by the output status in FIG. 3A, the procedure operation occurs when the closing operation is performed with respect to the movable handle 7 and the separation distance between the operation unit 72 and the handle body 62 is in the range of the second distance D2.

Figure 3B:
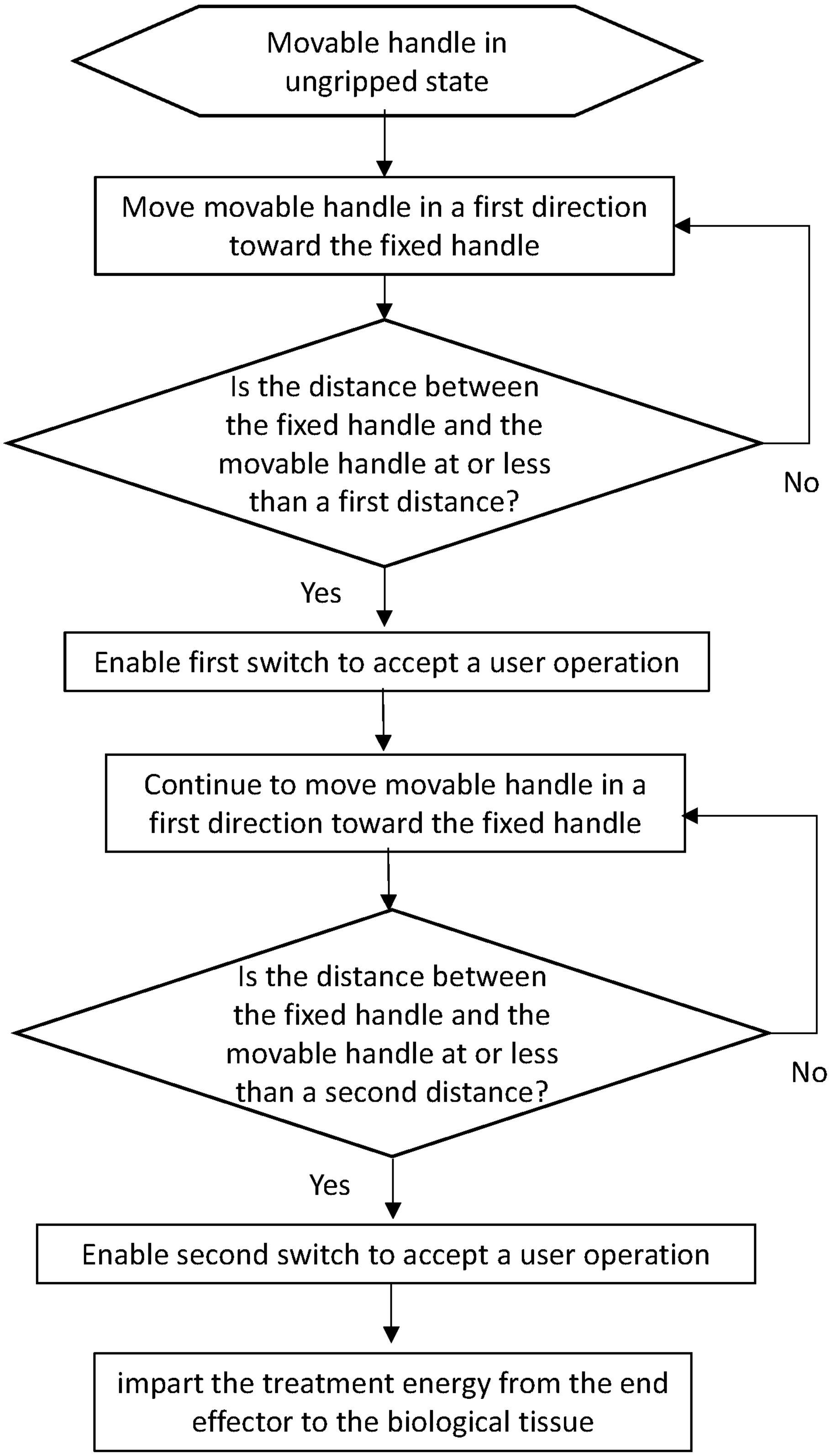

FIG. 3B is a process flow diagram illustrating the relationship between the operation state and the output state of the second switch when the closing operation is performed with respect to the movable handle.

On the Event where an Opening Operation is Performed on the Movable Handle

Figure 4A:
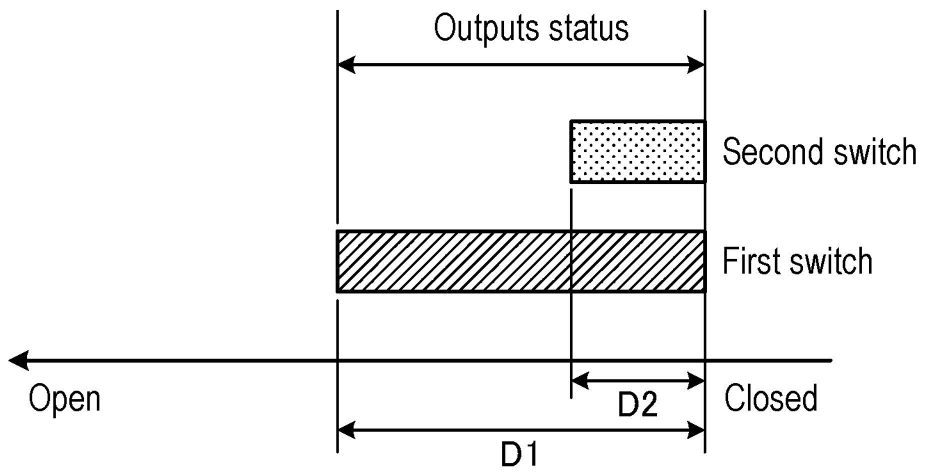
FIG. 4A is a diagram illustrating the relationship between the operation state and the output state of the second switch when the opening operation is performed with respect to the movable handle and FIG. 4B is a process flow diagram illustrating the relationship between the operation state and the output state of the second switch when the opening operation is performed with respect to the movable handle.

FIG. 4A is a diagram for explaining the relationship between the operation state and the output state of the first and second switches 81, 82 when the opening operation is performed with respect to the movable handle 7. When an opening operation is performed on the movable handle 7 and a separation distance between the movable handle 7 (operation unit 72) and the fixed handle 6 (handle body 62) becomes increasingly large and the separation distance becomes a second distance D2 or greater (FIG. 4A), the second switch 82 ends the acceptance of the treatment operation. In other words, when the operation unit 72 is moved in a direction away from the handle body 62, i.e., opening, when the separation distance between the operation unit 72 and the handle body 62 becomes a second distance D2 or greater, the second switch 82 is no longer enabled, i.e., turned OFF. In addition, when an opening operation is performed on the movable handle 7 and a separation distance between the movable handle 7 (operation unit 72) and the fixed handle 6 (handle body 62) becomes increasingly large and a separation distance becomes a first distance D1 or greater (where the separation distance is also larger than the second distance D2) (FIG. 4A), the first switch 81 ends the acceptance of the treatment operation. In other words, when the operation unit 72 is moved in a direction away from the handle body 62, i.e., opening, the first switch 81, when the separation distance between the operation unit 72 and the handle body 62 becomes the first distance D1 or greater, the first switch 81 is no longer enabled, i.e., turned OFF. Incidentally, the second distance D2 corresponds to the fourth distance according to the present invention and the first distance D1 corresponds to the third distance according to the present invention. When both the first and second switches 81 and 82 are no longer enabled to accept the procedure operation, then the processor 31 stops the operation of the power supply described above and terminates the application of the treatment energy to the target site from the end effector 13. That is, as shown by the output status in FIG. 4A, the procedure operation terminates when the opening operation is performed with respect to the movable handle 7 and the separation distance between the operation unit 72 and the handle body 62 is greater than the first distance D1.

Figure 4B:
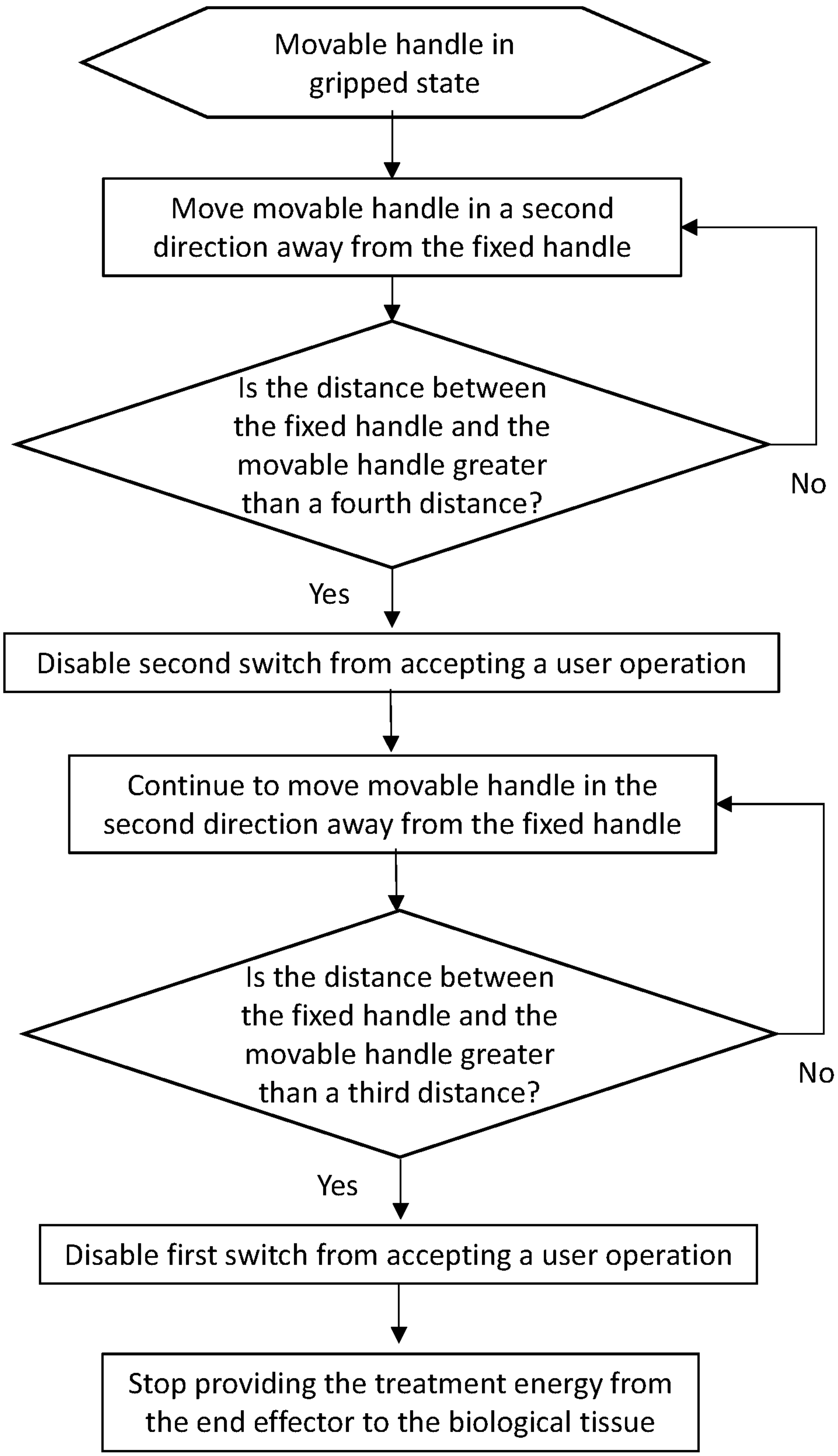

FIG. 4B is a process flow diagram illustrating the relationship between the operation state and the output state of the second switch when the opening operation is performed with respect to the movable handle.

In FIGS. 3A and 4A, the state in which the first switch 81 is ON is represented by a bar with a hatched line and the state in which the second switch 82 is ON is represented by a bar with dots.

As described above, the first switch 81 has a wider range (active range) in which the switch ON, as compared with the second switch 82. As the first switch 81, a switch having a wide active range can be used, for example, a photo interrupter, a rotary switch, or any of the switches provided with a contact on the side surface of the movable handle 7 can be employed.

According to the present embodiment described above, the following effects can be achieved. The treatment instrument 2 according to the present embodiment includes two switches, a first switch 81 and a second switch 81. The first switch 81 is provided inside the fixed handle 6 and, when the movable handle 7 is moved in a direction closer to the fixed handle 6 such that the distance between the fixed handle 6 and the movable handle 7 becomes the first distance D1, the first switch 81 is enabled to start receiving the treatment operation signal. The second switch 82 is provided in a state of being exposed to the outside of the fixed handle 6 (so as to be contactable by an operator) and, when the movable handle 7 is moved in a direction closer to the fixed handle 6 such that the distance between the fixed handle 6 and the movable handle 7 becomes the second distance D2 (where the second distance is different from the first distance D1), the second switch 82 is enabled to start receiving the treatment operation signal. Then, the processor 31 starts to impart procedure energy to the target site from the end effector 13 at the time when both of the first and second switches 81, 82 are enabled, e.g., start accepting the treatment operation (when both are switched on). Therefore, even when only one of the first and second switches 81, 82 is operated, the application of the procedure energy to the target site from the end effector 13 is not started. Accordingly, according to the treatment instrument 2 of the present embodiment, it is possible to avoid imparting the treatment energy to the target site unintentionally by an erroneous operation and imparting the treatment energy to the target site.

In addition, in the treatment tool 2 according to the present embodiment, when the movable handle 7 moves in a direction of being spaced apart from the fixed handle 6, the first switch 81 terminates the acceptance of the treatment operation at a time when the distance between the fixed handle 6 and the movable handle 7 becomes a first distance D1 or larger and the second switch 82 terminates the acceptance of the treatment operation at the time when the distance between the fixed handle 6 and the movable handle 7 becomes the second distance D2 or larger, where the second distance D2 is different from the first distance D1. When both of the first and second switches 81, 82 have terminated the acceptance of the treatment operation (at the time when both are switched off), then the processor 31 terminates the application of the procedure energy to the target site from the end effector 13.

As can be seen by comparing FIG. 3A and FIG. 4A, it is possible to widen the range of the output status when the opening operation is performed (shown in FIG. 4A) as compared to the range of the output status when the closing operation is performed (shown in FIG. 3A). Therefore, after an operator grips the operation portion 72 and the handle body 62, even when the separation distance between the operation portion 72 and the handle body 62 is somewhat increased by lessening the gripping force, it is possible to maintain the output status as ON. In other words, convenience can be improved.

Other Embodiments

While embodiments for carrying out the present invention have been described so far, the present invention is not to be limited only by the embodiments described above.

In the embodiment described above, the first switch 81 has a wider active range than the second switch 82, but the present invention is not limited thereto, conversely, the second switch 82 may have a wider active range than the first switch 81.

In the above-described embodiment, as the treatment instrument according to the present invention, a configuration is set to impart both ultrasonic energy and high frequency energy to the target site, but the present invention is not limited thereto. As the treatment instrument according to the present invention, it may be employed a configuration that imparts at least one treatment energy of ultrasonic energy, high frequency energy, and thermal energy to a target site. By "imparting heat energy to a target site" is meant that heat generated in a heater or the like is transmitted to a target site.

First Modification

In the above-described embodiment, the configuration according to the First Modification described below may be employed. Hereinafter, for convenience of explanation, the procedure system, the treatment instrument, and the end effector according to the First Modification will be described as a treatment system 1A, a treatment instrument 2A, and an end effector 13A, respectively.

Figure 5:
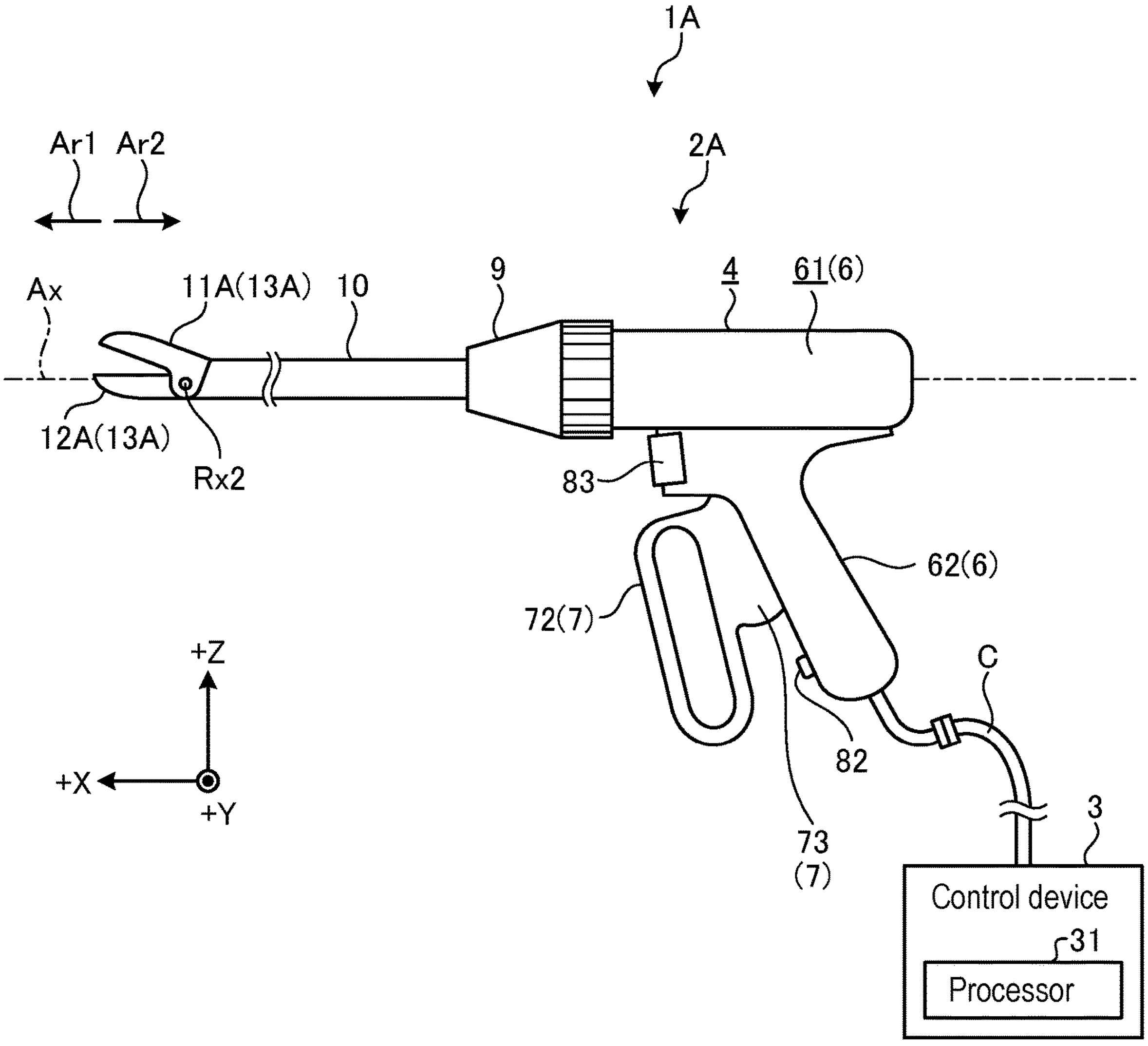
FIG. 5 is a diagram illustrating a first modification of the embodiment.
Figure 6:
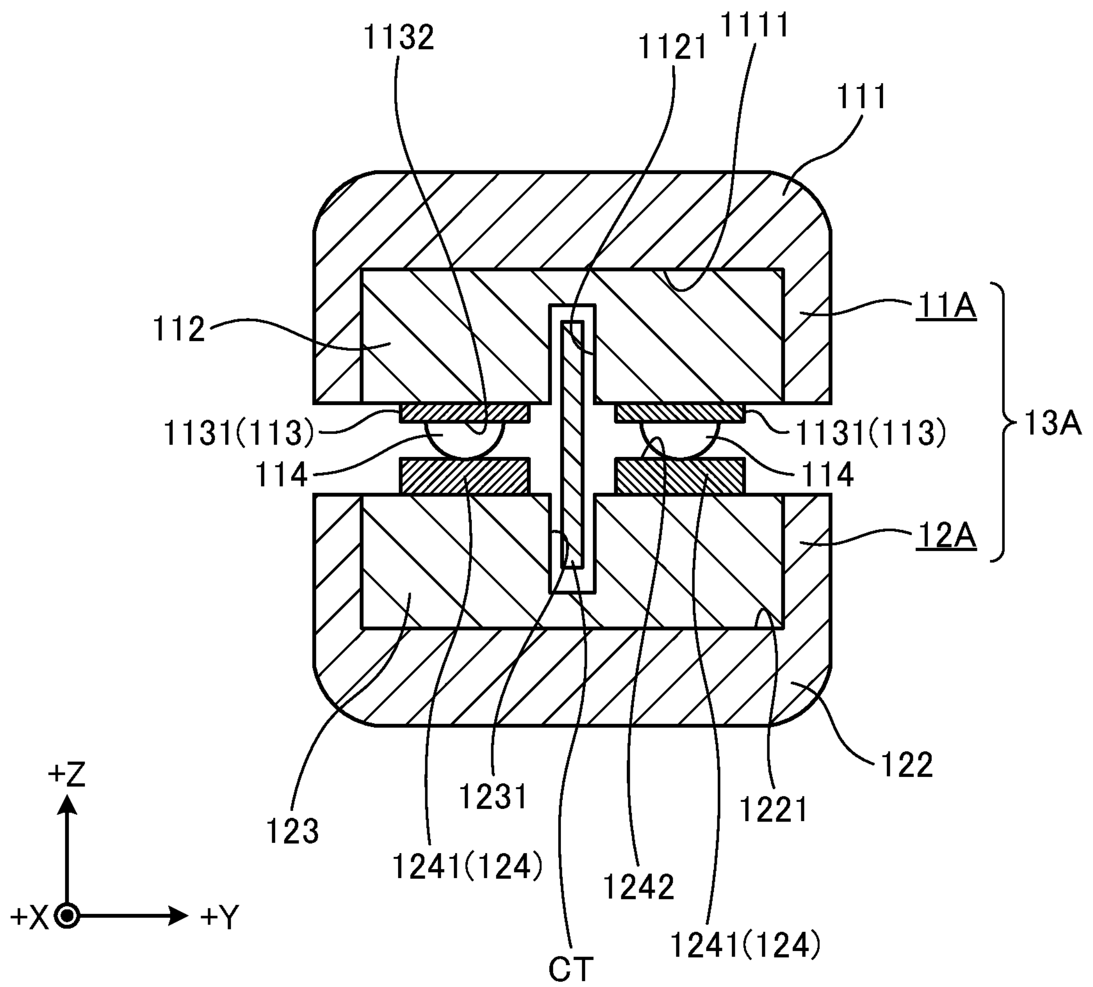
FIG. 6 is a diagram illustrating a first modification of the embodiment.

FIGS. 5 and 6 are views illustrating a First Modification of the embodiment. Specifically, FIG. 5 is a figure corresponding to FIG. 1, and is a figure showing the treatment system 1A according to the First Modification. FIG. 6 is a cross-sectional view of the end effector 13A according to the First Modification taken in a cross-section in the Y-Z plane.

As shown in FIG. 5 or FIG. 6, as compared to the end effector 13 described in the above-described embodiment, in the end effector 13A of the First Modification a first gripping piece 11A is employed in place of the jaw 11, and a second gripping piece 12A is employed in place of the vibration transmission member 12 (treatment portion 121). As shown in FIG. 6, the first gripping piece 11A comprises a first jaw 111, a first support member 112, a first bipolar electrode 113, and an contact portion 114.

The first jaw 111 is formed in an elongated shape extending along the central axis Ax. The end portion of the proximal end side Ar2 of the first jaw 111 is rotatably supported (with respect to the end portion of the distal end side Ar1 of the shaft 10) about a second rotational axis Rx2 extending in a direction perpendicular to the paper plane of FIG. 5. In order to have a predetermined rigidity, the first jaw 111 is composed of, for example, a metal material such as stainless steel or titanium. Then, the first jaw 111 (first gripping piece 11A) opens and closes with respect to second gripping piece 12A by operation of the opening and closing mechanism (not shown) in response to the closing operation and the opening operation to the movable handle 7 by an operator.

As shown in FIG. 6, the first jaw 111 includes a recess 1111. The recess 1111 is located in the center of the width direction of the first gripping piece 11A (in FIG. 6, the lateral direction) and opens toward the surface of the second gripping piece 12A (opens in −Z-axis side of the first jaw 111) and extends along the central axis Ax direction.

A first support member 112 is fitted into the recess 1111. The first support member 112 is an elongated flat plate extending along the central axis Ax and has an outer surface that is shaped substantially the same as the shape of the recess 1111. The first support member 112 is made of, for example, an insulating material having a low thermal conductivity such as PEEK (polyether ether ketone). The first support member 112 is disposed between the first bipolar electrode 113 and the first jaw 111 to electrically insulate the first jaw 111 from the first bipolar electrode 113.

As shown in FIG. 6, the first support member 112 includes cutter groove 1121, which is located in the width-direction substantially in a central portion of the surface of the first gripping piece 11A and opens toward the surface of the second gripping piece 12A and extends along the central axis Ax direction.

The first gripping piece 11A includes a first bipolar electrode 113. The first bipolar electrode 113 is composed of a conductive material such as copper and is a flat plate having a U-shape planarly surrounding the cutter groove 1121. The first bipolar electrode 113 is fixed to the surface of the first support member 112 that faces toward the second gripping piece 12A and is located in a position in which both ends of the U-shape are oriented toward the proximal side end Ar2. In the following, for convenience of explanation, in the first bipolar electrode 113, each portion extending along the central axis Ax is described as a pair of extending portions 1131 (see FIG. 6). Under the control of the processor 31, high-frequency power supplied from the power supply (not shown) passes between the first bipolar electrode 113 and the second bipolar electrode 124 (to be described later in connection with the second gripping piece 12A).

A coating material (not shown) having a non-stick property to a living body is attached to a surface 1132 of the first bipolar electrode 113 (FIG. 6) that faces toward the second gripping piece 12A. Contact portion 114 having a hemispherical shape and composed of an insulating material is provided on the surface 1132 of the first bipolar electrode 113. Then, the contact portion 114 abuts the second bipolar electrode 124 when the first gripping piece 11A closes with respect to the second gripping piece 12A. In other words, the contact portion 114 prevents the first and second bipolar electrodes 113,124 from being shorted to each other.

As shown in FIG. 6, the second gripping piece 12A comprises a second jaw 122, a second support member 123, and a second bipolar electrode 124. The second jaw 122 is formed in an elongated shape extending along the central axis Ax and extends from the distal end-side Ar1 of the shaft 10. As shown in FIG. 6, second jaw 122 includes a recess 1221. The recess 1221 is located in the center of the width direction of the second gripping piece 12A (in FIG. 6, the lateral direction) and opens toward the surface of the first gripping piece 11A (opens in +Z axial side of the second jaw 122) and extends along the central axis Ax direction.

A second support member 123 is fitted into the recess 1221. The second support member 123 is an elongated flat plate extending along the central axis Ax and has an outer surface that is shaped substantially the same as the shape of the recess 1221. The second support member 123 is made of, for example, an insulating material having a low thermal conductivity such as PEEK. The second support member 123 is disposed between the second bipolar electrode 124 and the second jaw 122 to electrically insulate the second jaw 122 from the second bipolar electrode 124.

As shown in FIG. 6, the second support member 123 includes cutter groove 1231, which is located in the width-direction substantially in a central portion of the surface of the second gripping piece 12A and opens toward the surface of the first gripping piece 11A and extends along the central axis Ax direction. Cutter groove 1231 is located in the width-direction so as to align with cutter groove 1121 in the first support member 112 when the first gripping piece 11A and the second gripping piece 12A are closed.

The second gripping piece 12A includes a second bipolar electrode 124. The second bipolar electrode 124 is composed of a conductive material such as copper and is a flat plate having a U-shape planarly surrounding the cutter groove 1231. The second bipolar electrode 124 is fixed to the surface of the second support member 123 that faces toward the first gripping piece 11A and is located in a position in which both ends of the U-shape are oriented toward the proximal side end Ar2. In the following, for convenience of explanation, in the second bipolar electrode 124, each portion extending along the central axis Ax is described as a pair of extending portions 1241 (see FIG. 6). Under the control of the processor 31, high-frequency power supplied from the power supply (not shown) passes between the first bipolar electrode 113 and the second bipolar electrode 124.

A coating material (not shown) having a non-stick property to the living body is attached to the surface 1242 of the second bipolar electrode 124 (FIG. 6) that faces toward the first gripping piece 11A.

When imparting high-frequency energy to the target site in a procedure, high-frequency power from the power supply (not shown) passes through the electric cable C and is supplied between the two bipolar electrodes 113,124 under the control of the processor 31. Thus, a high frequency current flows through the target site grasped between the first and second bipolar electrodes 113,124. In other words, the subject site is imparted with high frequency energy.

Further, in the First Modification and as shown in FIG. 6, the cutter CT located in the cutter groove 1121, 1231 of end effector 13A moves forward and backward along the central axis Ax direction in accordance with the operation to the operation lever 83 (FIG. 5) by an operator. That is, the target site grasped between the first and second gripping pieces 11A,12A is dissected by the advancing and retracting movement of the cutter CT.

Even when the treatment instrument 2A according to the First Modification described above is employed, the same effect as in the above-described embodiment is achieved.

Second Modification

In the above-described embodiment, the configuration according to the Second Modification described below may be employed. Hereinafter, for convenience of description, a rotary knob according to the Second Modification will be described as a rotary knob 300.

Figure 7:
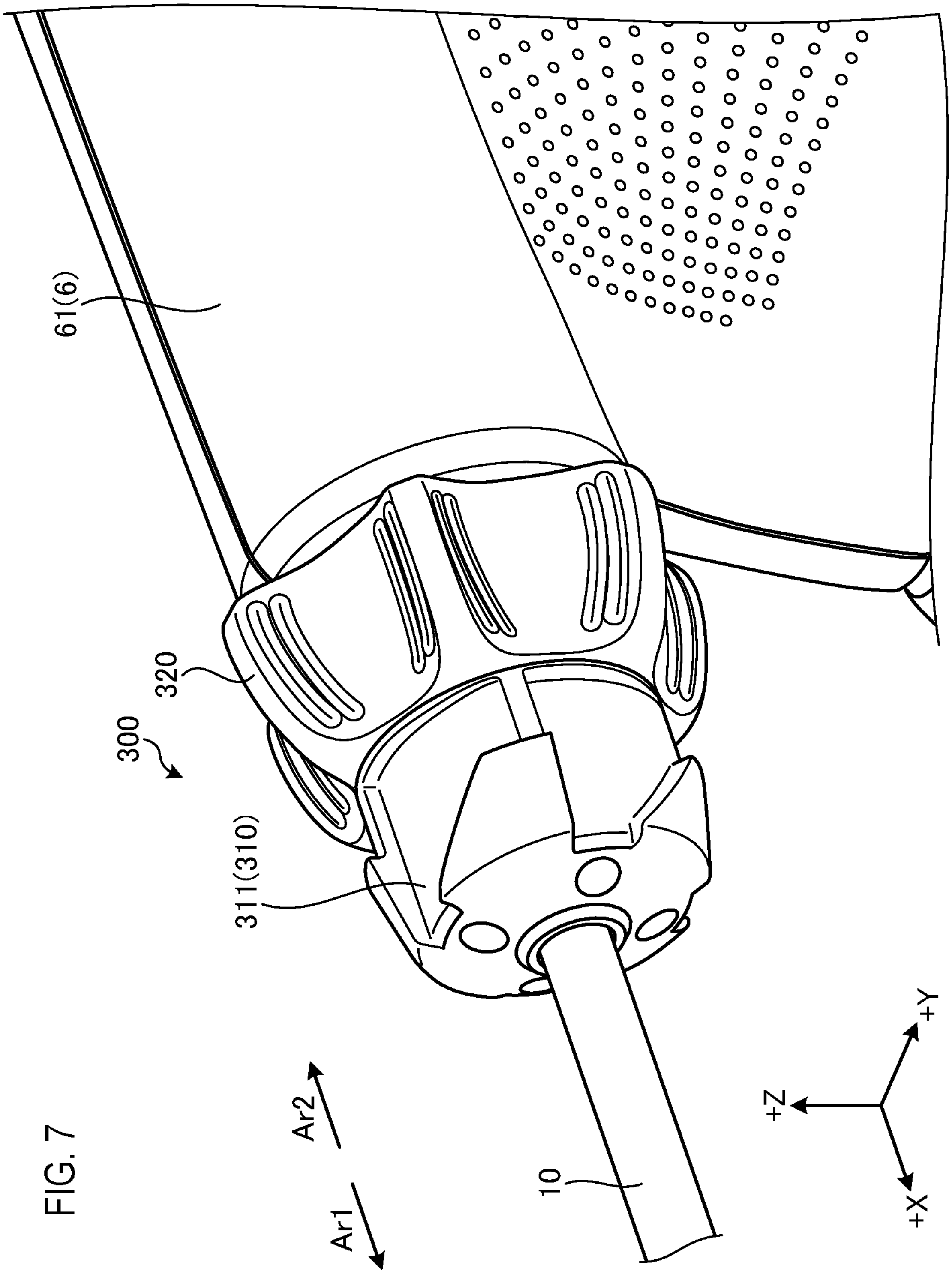
FIG. 7 is a diagram illustrating a second modification of the embodiment.
Figure 8A:
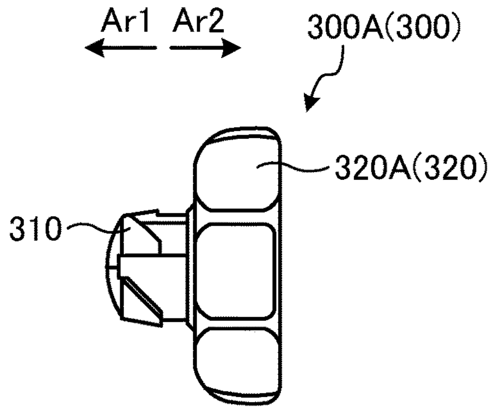
FIG. 8A is a diagram illustrating a second modification of the embodiment.
Figure 8B:
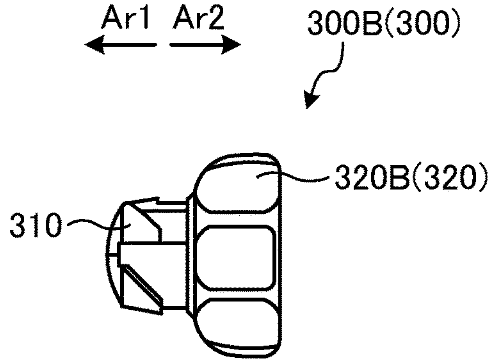
FIG. 8B is a diagram illustrating a second modification of the embodiment.
Figure 8C:
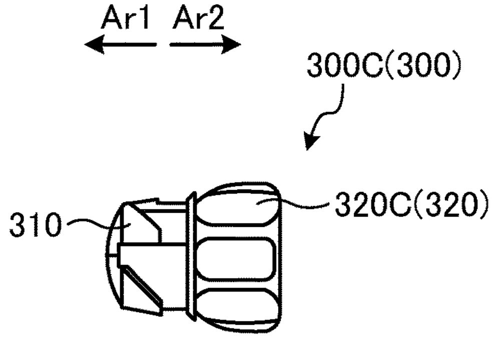
FIG. 8C is a diagram illustrating a second modification of the embodiment.
Figure 9:
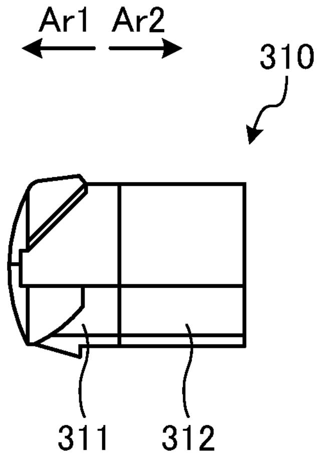
FIG. 9 is a diagram illustrating a second modification of the embodiment.
Figure 10A:
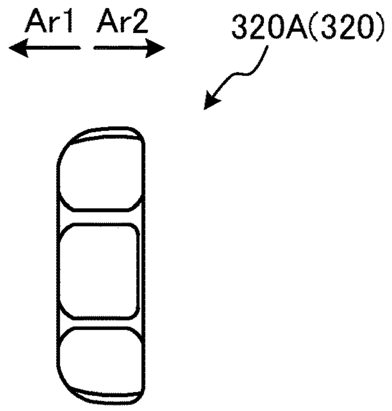
FIG. 10A is a diagram illustrating a second modification of the embodiment.
Figure 10B:
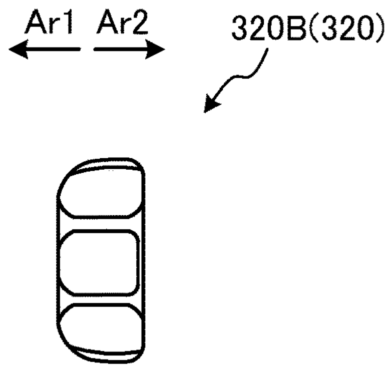
FIG. 10B is a diagram illustrating a second modification of the embodiment.
Figure 10C:
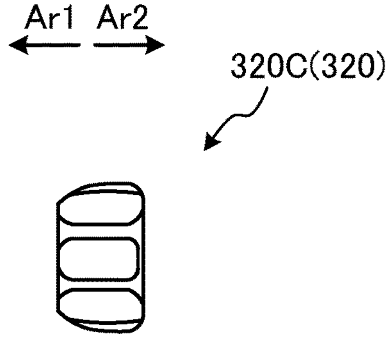
FIG. 10C is a diagram illustrating a second modification of the embodiment.

FIGS. 7 to 10 are views illustrating the Second Modification of the embodiment. Specifically, FIG. 7 is a perspective view of rotary knob 300. FIGS. 8A to 8C are views of different embodiments of the rotary knob 300 viewed from the side. FIG. 9 is a view of the engagement portion 310 of the rotary knob 300 viewed from the side. FIGS. 10A to 10C are views of the rotation operation unit 320 of the different embodiments of the rotary knob 300 from the side.

Here, the vibration transmission member 12 and the ultrasonic vibrator 52 are connected to each other by a screwed structure. Specifically, the vibration transmission member 12 is connected to the ultrasonic vibrator 52 by rotating the rotary knob 300 about the central axis Ax together with the vibration transmission member 12. When connecting the vibration transmission member 12 and the ultrasonic vibrator 52 to each other by rotating the rotary knob 300 about the central axis Ax, a tool such as a torque wrench (not shown) can be used.

As shown in FIGS. 7 to 10, the rotary knob 300 includes an engagement portion 310 that engages with the torque wrench and a rotation operation unit 320 that receives a rotation operation by an operator. In the Second Modification, the engagement portion 310 and the rotation operation unit 320 are separate from each other. Furthermore and as shown in FIG. 9, the only one type of engagement portion 310 is provided (see FIG. 9), while three types of the rotation operation unit 320 are provided—first to third rotation operation units 320A, 320B, 320C (see FIGS. 10A to 10C). Only one type of the three types of the rotation operation units 320 is used, i.e., one of the first to third rotation operation units 320A, 320B, 320C. That is, the rotary knob 300 is combined with the engagement portion 310 and one of the first to third rotation operation units 320A, 320B, 320C to form, in combination, three types of rotary knobs 300A, 300B, 300C (see FIGS. 8A to 8C).

Engagement portion 310 has a substantially cylindrical shape extending along the central axis Ax. As shown in FIG. 9, the engagement portion 310 has an engaged portion body 311 that is a portion to be engaged with respect to the torque wrench. The engaged portion body 311 is connected to a connecting portion 312 that connects to the rotation operation unit 320. In the engagement portion 310, the engaged portion body 311 is located on the distal end side Ar1 and the connecting portion 312 is located on the proximal end side Ar2. The engagement portion 310 and the connecting portion 312 can be integrally configured.

Rotation operation unit 320 has an annular shape around the central axis Ax, for example, connected to the outer peripheral surface of the connecting portion 312 by a connection structure such as a snap fit. Note that the first to third rotation operation units 320A, 320B, 320C differ only in outer diameter dimensions.

For example, at the time of product shipment of the treatment instrument, only the engagement portion 310 is attached to the treatment instrument. On the other hand, the first to third rotation operation units 320A, 320B, 320C are not attached to the treatment instrument and are packaged with the treatment instrument. Here, the user who has received the product selects the rotation operation unit 320 having the outer diameter dimension that is considered to be easy for the user to perform the rotation operation from among the first to third rotation operation units 320A, 320B, 320C. Then, with the shaft 10 inserted in the engagement portion 310, the rotation operation unit 320 is connected to the outer peripheral surface of the connecting portion 312.

Here, a memory (not shown) for storing information corresponding to the outer diameter dimensions of the first to third rotation operation units 320A, 320B, 320C is provided in the first to third rotation operation units 320A, 320B, 320C. Further, the processor 31 recognizes the rotation operation unit 320 connected to the engagement portion 310 from among the first to third rotation operation units 320A, 320B, 320C by reading the information stored in the memory, which information is passed through the electric cable C. Then, the processor 31 changes the initial function according to the recognized rotation operation unit 320. In other words, the processor 31 performs control corresponding to the recognized rotation operation unit 320.

DESCRIPTION OF SYMBOLS

1, 1A treatment system
2, 2A treatment instrument
3 Control device
4 Handpiece
5 Ultrasonic transducer
6 Fixed handle
7 Movable handle
9 Rotary knob
10 Shaft
11 Jaw
11A first gripping piece
12 Vibration transmission member
12A second gripping piece

13, 13A end effector
31 Processor
51 TD case
52 Ultrasonic vibrator
61 Case body
62 Handle body
71 Handle base
72 Operation unit
73 Connecting portion
81 First switch
82 Second switch
83 Operation lever
111 First jaw
112 First support member
113 First bipolar electrode
114 Contact portion
121 Treatment portion
122 Second jaw
123 Second support member
124 Second bipolar electrode
300, 300A, 300B, 300C rotary knob
310 Engagement portion
311 Engaged portion body
312 Connecting portion
320 Rotation operation unit
320A first rotation operation unit
320B second rotation operation unit
320C third rotation operation unit
1111 Recess
1121 Cutter groove
1131 Extending portion
1132 Surface
1221 Recess
1231 Cutter groove
1241 Extending portion
1242 Surface
Ar1 distal end side
Ar2 proximal end side
Ax central axis
C Electrical cable
CT cutter
D1 First distance
D2 Second distance
Rx1 first rotational axis
Rx2 second rotational axis

What is claimed is:

1. A treatment instrument, comprising:
an end effector configured to supply a treatment energy to a biological tissue;
a fixed handle configured to be grasped by an operator;
a movable handle configured to open and close the end effector by moving relative to the fixed handle;
a first switch provided in an interior of the fixed handle, the first switch configured to allow supply of the treatment energy from the end effector to the biological tissue when the movable handle is in contact with the first switch; and
a second switch provided on an outer surface of the fixed handle, the second switch configured to supply the treatment energy from the end effector to the biological tissue when the movable handle is in contact with the first switch and the second switch.

2. The treatment instrument according to claim 1, wherein the movable handle is in contact with the first switch when a distance between the fixed handle and the movable handle becomes a first distance,
wherein the movable handle is in contact with the second switch when the distance between the fixed handle and the movable handle becomes a second distance, and
wherein that the second distance is different from the first distance.

3. The treatment instrument according to claim 2, wherein the first distance is larger than the second distance.

4. The treatment instrument according to claim 3, wherein the movable handle is not in contact with the first switch when the distance between the fixed handle and the movable handle becomes a third distance,
wherein the movable handle is not in contact with the second switch when the distance between the fixed handle and the movable handle becomes a fourth distance, and wherein the fourth distance is different from the third distance.

5. The treatment instrument according to claim 4, wherein the third distance is larger than the fourth distance.

6. The treatment instrument according to claim 1, wherein the first switch is one of the following:
a photo interrupter,
a rotary switch, and
a switch provided with a contact on a side surface of the movable handle.

7. A treatment system, comprising:
a treatment instrument configured to treat a biological tissue; and
a control device having a processor that controls an operation of the treatment instrument;
wherein the treatment instrument includes:
an end effector configured to supply a treatment energy to a biological tissue;
a fixed handle configured to be grasped by an operator;
a movable handle configured to open and close the end effector by moving relative to the fixed handle;
a first switch provided in an interior of the fixed handle, the first switch configured to allow supply of the treatment energy from the end effector to the biological tissue when the movable handle is in contact with the first switch; and
a second switch provided on an outer surface of the fixed handle, the second switch configured to supply the treatment energy from the end effector to the biological tissue when the movable handle is in contact with the first switch and the second switch,
wherein the movable handle is in contact with the first switch when a distance between the fixed handle and the movable handle becomes a first distance,
wherein the movable handle is in contact with the second switch when the distance between the fixed handle and the movable handle becomes a second distance,
wherein that the second distance is different from the first distance, and
wherein the processor supplies the treatment energy from the end effector to the biological tissue when the movable handle is in contact with both of the first switch and the second switch.

8. The treatment system according to claim 7, wherein the first distance is larger than the second distance.

9. The treatment system according to claim 7, wherein the movable handle is not in contact with the first switch when the distance between the fixed handle and the movable handle becomes a third distance,
wherein the movable handle is not in contact with the second switch when the distance between the fixed handle and the movable handle becomes a fourth distance, wherein the fourth distance is different from the third distance, and wherein the processor stops supplying the treatment energy from the end effector to the biological tissue when the movable handle is not in contact with the second switch.

10. The treatment system according to claim 9, wherein the third distance is larger than the fourth distance.

11. A control method performed by a processor of a control device that controls an operation of a treatment instrument, wherein the treatment instrument includes:

an end effector configured to supply a treatment energy to a biological tissue;

a fixed handle configured to be grasped by an operator;

a movable handle configured to open and close the end effector by moving relative to the fixed handle;

a first switch provided in an interior of the fixed handle, the first switch configured to allow supply of the treatment energy from the end effector to the biological tissue when the movable handle is in contact with the first switch; and a second switch provided on an outer surface of the fixed handle, the second switch configured to supply the treatment energy from the end effector to the biological tissue when the movable handle is in contact with the first switch and the second switch, the control method comprising:

moving the movable handle in a first direction toward the fixed handle to contact the first switch, wherein the movable handle contacts the first switch when a distance between the fixed handle and the movable handle becomes a first distance;

moving the movable handle in the first direction toward the fixed handle to contact the second switch, wherein the movable handle contacts the second switch when the distance between the fixed handle and the movable handle becomes a second distance; and supplying the treatment energy from the end effector to the biological tissue when the movable handle is in contact with both of the first switch and the second switch, wherein that the second distance is different from the first distance.

12. The control method according to claim 11, further comprising:

moving the movable handle in a second direction away from the fixed handle to not contact the first switch, wherein the movable handle does not contact the first switch when the distance between the fixed handle and the movable handle becomes a third distance;

moving the movable handle in the second direction away from the fixed handle to not contact the second switch, wherein the movable handle does not contact the second switch when the distance between the fixed handle and the movable handle becomes a fourth distance; and stopping supplying the treatment energy from the end effector to the biological tissue when the movable handle is in not in contact with both of the first switch and the second switch, wherein the fourth distance is different from the third distance.

13. The treatment instrument according to claim 2, wherein the first switch is configured to not allow supply of the treatment energy from the end effector to the biological tissue when the movable handle is not in contact with the first switch, and wherein the second switch is configured to not supply the treatment energy from the end effector to the biological tissue when the movable handle is not in contact with the first switch and the second switch.

14. The treatment instrument according to claim 1, wherein contact between the movable handle and the first switch is direct contact, wherein contact between the movable handle and the second switch is direct contact, and wherein the treatment energy from the end effector to the biological tissue is supplied when the movable handle is in direct contact with the first switch and the second switch.

15. The treatment instrument according to claim 1, wherein contact between the movable handle and the first switch is a first portion of the movable handle in direct contact with the first switch, wherein contact between the movable handle and the second switch is a second portion of the movable handle in direct contact with the second switch, wherein the first portion of the movable handle is different from the second portion of the movable handle, and wherein the treatment energy from the end effector to the biological tissue is supplied when the first portion of the movable handle is in direct contact with the first switch and the second portion of the movable handle is in direct contact with the second switch.

16. A treatment system, comprising:

the treatment instrument according to claim 1; and a control device having a processor that controls an operation of the treatment instrument, wherein the processor is configured to:

detect an operation state of the first switch and an operation state of the second switch, and operate a power supply according to a detected operation state of the first switch and a detected operation state of the second switch, and wherein the power supply is configured to supply the treatment energy to the end effector.

17. The treatment system according to claim 16, wherein when the detected operation state of the first switch corresponds to the movable handle being in contact with the first switch and the detected operation state of the second switch corresponds to the movable handle being in contact with the second switch, the processor supplies the treatment energy to the end effector.

18. The treatment system according to claim 17, wherein when the detected operation state of the first switch corresponds to the movable handle not being in contact with the first switch and the detected operation state of the second switch corresponds to the movable handle not being in contact with the second switch, the processor does not supply the treatment energy to the end effector.

19. The control method according to claim 11, wherein contact between the movable handle and the first switch is direct contact, wherein contact between the movable handle and the second switch is direct contact, and wherein the treatment energy from the end effector to the biological tissue is supplied when the movable handle is in direct contact with the first switch and the second switch.

20. The control method according to claim 11, wherein contact between the movable handle and the first switch is a first portion of the movable handle in direct contact with the first switch, wherein contact between the movable handle and the second switch is a second portion of the movable handle in direct contact with the second switch, wherein the first portion of the movable handle is different from the second portion of the movable handle, and wherein the treatment energy from the end effector to the biological tissue is supplied when the first portion of the movable handle is in direct contact with the first switch and the second portion of the movable handle is in direct contact with the second switch.

* * * * *